(12) United States Patent
Roche et al.

(10) Patent No.: US 10,093,971 B2
(45) Date of Patent: *Oct. 9, 2018

(54) HEATING MECHANISM FOR DNA AMPLIFICATION, EXTRACTION OR STERILIZATION USING PHOTO-THERMAL NANOPARTICLES

(71) Applicant: The Royal Institution for the Advancement of Learning/McGill University, Montreal (CA)

(72) Inventors: Philip Roche, Mount Royal (CA); Andrew Kirk, Outremont (CA); Lenore Beitel, Montreal (CA); Miltiadis Paliouras, Laval (CA); Mark Trifiro, Montreal (CA); Vamsy Chodavarapu, Brossard (CA); Mohamed Najih, Sorel-tracy (CA); Joachim Thiemann, Kitchener (CA)

(73) Assignee: THE ROYAL INSTITUTION FOR THE ADVANCEMENT OF LEARNING/MCGILL UNIVERSITY, Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/720,196

(22) Filed: Sep. 29, 2017

(65) Prior Publication Data
US 2018/0037933 A1    Feb. 8, 2018

Related U.S. Application Data

(63) Continuation of application No. 13/943,312, filed on Jul. 16, 2013, now Pat. No. 9,816,132.

(60) Provisional application No. 61/737,175, filed on Dec. 14, 2012.

(51) Int. Cl.
*C12Q 1/68*    (2018.01)
*C12N 15/10*   (2006.01)
*C12Q 1/686*   (2018.01)

(52) U.S. Cl.
CPC ......... *C12Q 1/686* (2013.01); *C12N 15/1006* (2013.01)

(58) Field of Classification Search
None
See application file for complete search history.

(56) References Cited

U.S. PATENT DOCUMENTS 7,998,672 B2    8/2011  Roper
9,816,132 B2 *  11/2017 Roche ............... C12N 15/1006
2008/0131939 A1 6/2008  Roper

FOREIGN PATENT DOCUMENTS

EP      2481817 A1     8/2012
WO      2013113910 A1  8/2013

OTHER PUBLICATIONS

Bedford EE, Spadavecchia J, Pradier CM, Gu FX. Surface plasmon resonance biosensors incorporating gold nanoparticles. Macromol Biosci. Jun. 2012; 12(6):724-39. Epub Mar. 13, 2012. (Year: 2012).*
Cai, M., Li, F., Zhang, Y. and Wang, Q., One-pot polymerase chain reaction with gold nanoparticles for rapid and ultrasensitive DNA detection. Nano Research, 2010, 3(8):557-563. (Year: 2010).*
Gao, Xiang, Qingdai Liu, Yi Zhao, Zhenjing Li, Yurong Wang, Dongsheng Zhou, Kan Jiang, and Cheng Luo. Influences of gold and silver nanoparticles in loop-mediated isothermal amplification reactions. Journal of Experimental Nanoscience 9, 2014, (9): 922-930. Epub Dec. 10, 2012. (Year: 2012).*
Mi, LiJuan, HongPing Zhu, XiaoDong Zhang, Jun Hu, and ChunHai Fan. Mechanism of the interaction between Au nanoparticles and polymerase in nanoparticle PCR. Chinese Science Bulletin 2007, 52(17): 2345-2349. (Year: 2007).*
Miyako, E., Nagata, H., Hirano, K., Makita, Y., Nakayama, K. I., & Hirotsu, T. Near-infrared laser-triggered carbon nanohorns for selective elimination of microbes. Nanotechnology, 2007. 18(47), 475103, pp. 1-7. (Year: 2007).*
Miyako et al. Carbon Nanotube—Polymer Composite for Light-Driven Microthermal Control. Angewandte Chemie International Edition. 2008. 47(19) 3610-3613. (Year: 2008).*
Miyako, et al. Supplementary, S1-S4. Angewandte Chemie International Edition. 2008. 47(19) 3610-3613. (Year: 2008).*
Miyako, Eijiro, Hideya Nagata, Ken Hirano, and Takahiro Hirotsu. Laser-triggered carbon nanotube microdevice for remote control of biocatalytic reactions. Lab on a chip. 2009. 9(6): 788-794. (Year: 2009).*
Sun, Xiaohong, Qian Xu, Yingjie Pan, Weiqing Lan, Yong Zhao, and Vivian CH Wu. A loop-mediated isothermal amplification method for rapid detection of Vibrio parahaemolyticus in seafood. Annals of microbiology, 2012, 62(1): 263-271 (Year: 2012).*
Link, S. et al., "Shape and size dependence of radiative, non-radiative and photothermal properties of gold nanocrystals," Int. Rev. Phys. Chem. 2000, vol. 19(3), p. 409-453.

(Continued)

*Primary Examiner* — Angela Marie Bertagna
*Assistant Examiner* — Olayinka A Oyeyemi
(74) *Attorney, Agent, or Firm* — Benoit & Cote Inc.; Mathieu Miron

(57) ABSTRACT

A heating mechanism for use in DNA applications such as DNA amplification, extraction and sterilization is provided. Nanoparticles having photo-thermal properties are put in contact with a reaction mixture and irradiated with an activation light beam to activate these photo-thermal properties, thereby releasing heat. Nanoparticles of several types may be used. Use of the same nanoparticles or of different one to monitor the reaction using a different light beam is also presented.

16 Claims, 8 Drawing Sheets
Specification includes a Sequence Listing.

(56) References Cited

OTHER PUBLICATIONS

Deng, H. et al., "Gold nanoparticles with asymmetric polymerase chain reaction for colorimetric detection of DNA sequence," Analytical Chemistry, vol. 84, p. 1253-1258, Jan. 13, 2012.
Roper, D.K. et al., "Microscale heat transfer transduced by surface plasmon resonant gold nanoparticles," J. Phys, Chem C Nanomater Interfaces, vol. 111(9), p. 3636-3641, Sep. 2007.
Sipova, H. et al., "Surface plasmon resonance sensing of nucleic acids: A review," Analytica Chimica Acta, vol. 773, p. 9-23, Apr. 22, 2013.
Roche, Philip et al., Demonstration of a plasmonic thermocycler for the amplification of human androgen receptor DNA, Analyst, 2012. pp. 4475-4481, 137, The Royal society of Chemistry, UK.
Huang, Yi-You et al., A protein detection technique by using surface plasmon resonance (SPR) with rolling circle amplification (RCA) and nanogold-modified tags, Biosensors and Bioelectronics, 2007, pp. 980-985, 22, Elsevier B.V., Philadelphia.
Xiang, Yang et al., Isothermal detection of multiple point mutations by a surface plasmon resonance biosensor with Au nanoparticles enhanced surface-anchored rolling circle amplification, Biosensors and Bioelectronics, 2013, pp. 442-449, 49, Elsevier B.V., Philadelphia.
Polo, Ester et al., Plasmonic-driven thermal sensing: ultralow detection of cancer markers, Chem. Commun., 2013, pp. 3676-3678,49, The Royal Society of Chemistry, UK.
Richardson, H. H., Carlson, M. T., Tandler, P. J., Hernandez, P., & Govorov, A.O. (2009). Experimental theoretical studies of light-to-heat conversion and collective heating effects in metal nanoparticle solutions. Nano letters, 9(3), 1139-1146.
Li M, Lin YC, Wu CC, Liu HS. Enhancing the efficiency of a PCR using gold nanoparticles. Nucleic Acids Res. Nov. 27, 2005; 33(21):1-10.
Li H, Huang J, Lv J, An H, Zhang X, Zhang Z, Fan C, Hu J. Nanoparticle PCR: nanogold-assisted PCR with enhanced specificity. Angew Chem Int Ed Engl. Aug. 12, 2005; 44(32):5100-3.
Akilany, A. M., & Murphy, C.J. (2010). Toxicity and cellular uptake of gold nanoparticles: what we have learned so far?. Journal of nanoparticle research, 12(7), 2313-2333.
Belder D, Ludwig M. Surface modification in microchip electrophoresis. Electrophoresis. Nov. 2003; 24(21):3595-606. Review.
Jain PK, Huang X, El-Sayed IH, El-Sayed MA. Noble metals on the nanoscale: optical and photothermal properties and some applications in imaging, sensing, biology, and medicine. Acc Chem Res. Dec. 2008 41(12):1578-86.
Jain, P.K., Huang, X., El-Sayed, I.H., & El-Sayed, M. A. Review of some interesting surface plasmon resonance-enhanced properties of noble metal nanoparticles and their applications to biosystems. Plasmonics, 2007, 2(3), 107-118.
Hrelescu, C., Stehr, J., Ringler, M., Sperling, R. A., Parak, W.J., Klar, T.A., & Feldman, J. (2010). DNA melting in gold nanostove clusters. The Journal of Physical Chemistry C, 114(16), 7401-7411.
Lassiter JB, Knight MW, Mirin NA, Halas NJ. Reshaping the plasmonic properties of an individual nanoparticle. Nano Lett. Dec. 2009;9(12):4326-32.
Lee, K. S., & El-Sayed, M.A. (2006). Gold and silver nanoparticles in sensing and imaging: sensitivity of plasmon response to size, shape, and metal composition. The journal of Physical Chemistry B, 110(39), 19220-19225.
Lou, X., & Zhang, Y. (2013). Mechanism studies on nanoPCR and applications of gold nanoparticles in genetic analysis. ACS applied materials & interfaces, 5(13), 6276-6284.
Pissuwan D, Valenzuela S, Cortie MB. Prospects for gold nanorod particles in diagnostic and therapeutic applications. Biotechnol Genet Eng Rev. 2008; 25: 93-112. Review.
Stehr J, Hrelescu C, Sperling RA, Raschke G, Wunderlich M, Nichtl A, Heindl D, Kurzinger K, Parak WJ, Klar TA, Feldmann J. Gold nanostoves for microsecond DNA melting analysis. Nano Lett. Feb. 2008; 8(2):619-23. Epub Jan. 26, 2008.
Warshavski, O., Minai, L, Bisker, G., & Yelin, D. (2011). Effect of single femtosecond pulses on gold nanoparticles. The Journal of Physical Chemistry C, 115(10), 3910-3917.
Xia, Y. M., Hua, Z. S., Srivannavit, O., Ozel, A. B., & Gulari, E. (2007). Minimizing the surface effect of PDMS-glass microchip on polymerase chain reaction by dynamic polymer passivation. Journal of Chemical Technology and Biotechnology, 82(1), 33-38.
Fang, C., Shao, L, Zhao, Y., Wang, J., & Wu, H. A gold nanocrystal/poly(dimethylsiloxane) composite for plasmonic heating on microfluidic chips. Advanced Materials, 2012. 24(1):94-98.
Miyako, E., Nagata H., Hirano, K., Makita, Y., Nakayama, K.I., & Hirotsu, T. Near-infared laser-triggered carbon nanohorns for selective elimination of microbes. Nanotechnology, 2007. 18(47), 475103.
Miyako, Eijiro, et al. Carbon Nanotube-Polymer Composite for Light-Driven Microthermal Control. Angewandte Chemie International Edition. 2008. 47(19) 3610-3613.
2008—Supporting info for Miyako, Eijiro, et al. Carbon Nanotube-Polymer Composite for Light-Driven Microthermal Control. Angewandte Chemie International Edition. 2008. 47(19) 3610-3613.
Miyako, Eijiro, Hideya Nagata, Ken Hirano, and Takahiro Hirotsu. Laser-triggered carbon nanotube microdevice for remote control of biocatalytic reactions. Lab on a chip. 2009. 9(6): 788-794.
Li Z, Wang P, Tong L, Zhang L. Gold nanorod-facilitated localized heating of droplets in microfluidic chips. Opt Express. Jan. 14, 2013;21(1):1281-6.

* cited by examiner

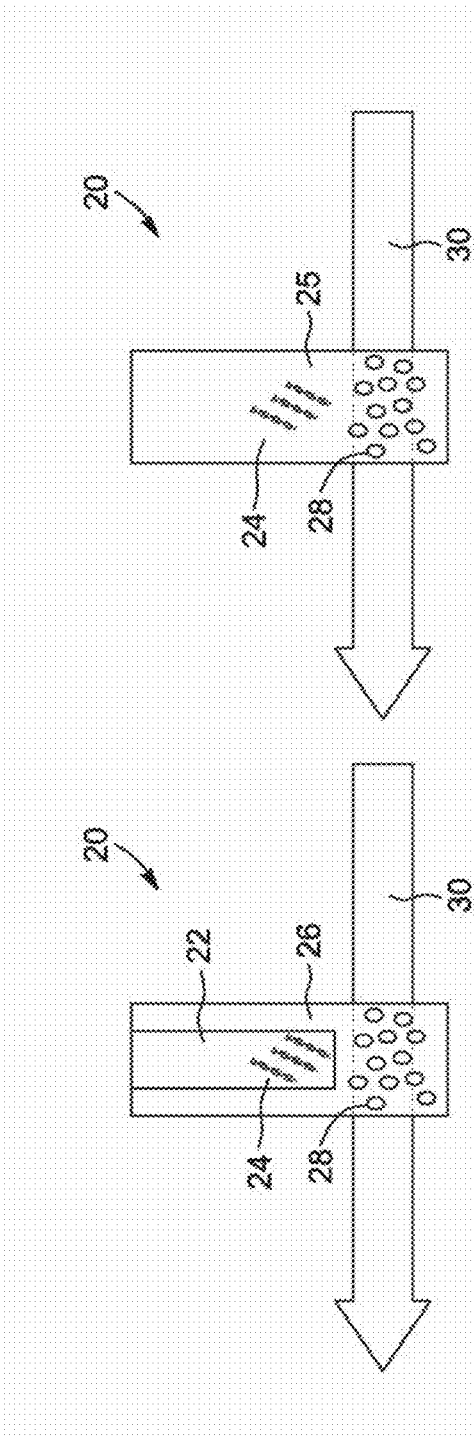
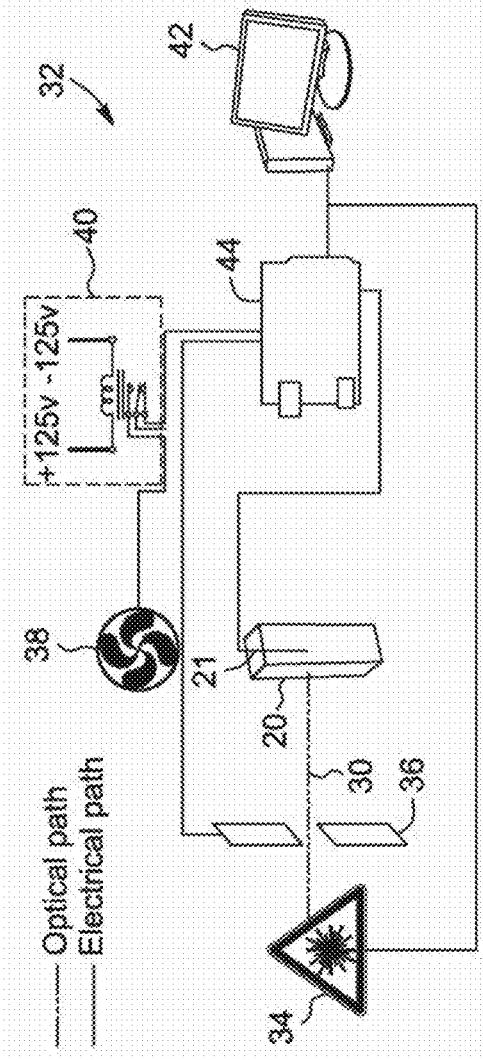

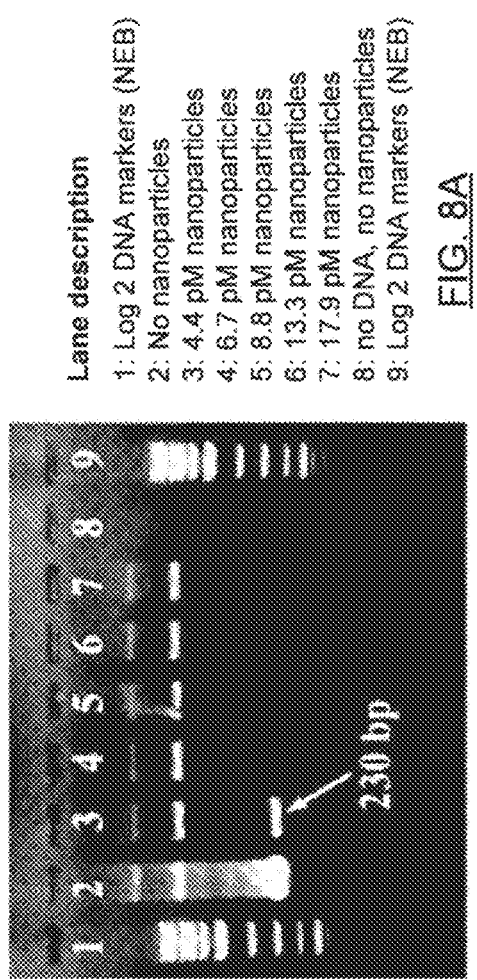
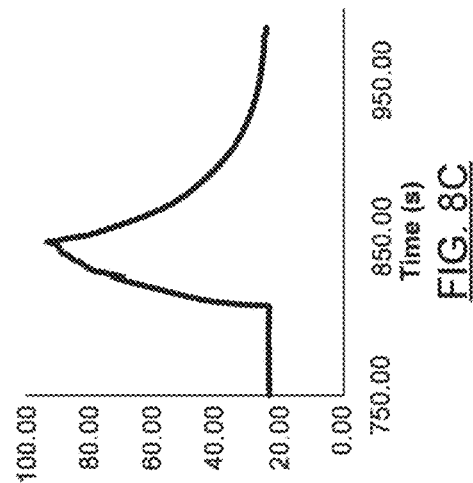
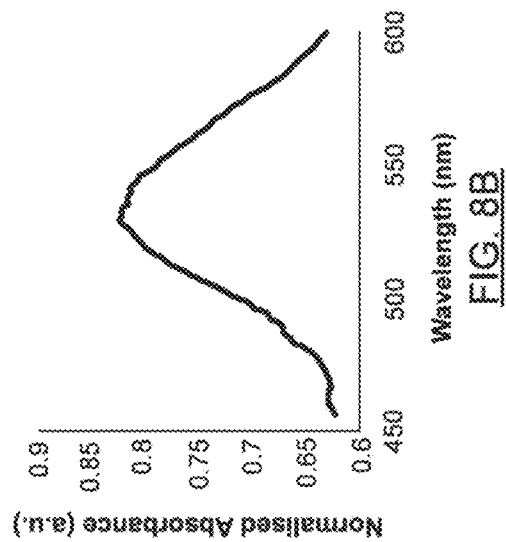
FIG. 8A
Lane description
1: Log 2 DNA markers (NEB)
2: No nanoparticles
3: 4.4 pM nanoparticles
4: 6.7 pM nanoparticles
5: 8.8 pM nanoparticles
6: 13.3 pM nanoparticles
7: 17.9 pM nanoparticles
8: no DNA, no nanoparticles
9: Log 2 DNA markers (NEB)
FIG. 8B
FIG. 8C

HEATING MECHANISM FOR DNA AMPLIFICATION, EXTRACTION OR STERILIZATION USING PHOTO-THERMAL NANOPARTICLES

RELATED PATENT APPLICATION

This application is filed under 37 CFR 1.53(b) as a continuation application. This application claims priority under 35 USC § 120 of U.S. patent application Ser. No. 13/943,312, filed Jul. 16, 2013, which claims priority from and the benefit of U.S. Provisional Patent Application No. 61/737,175, filed on Dec. 14, 2012, the specifications of which are hereby incorporated by reference in their entireties.

FIELD OF THE INVENTION

The present description relates to processes involving DNA and more particularly concerns a heating method for performing such molecular biological techniques using nanoparticles having photo-thermal properties.

BACKGROUND

Polymerase Chain Reaction (PCR) is a DNA amplification technique which is essential to genetics, and particularly in next generation sequencing, where amplification of the quantity of starting DNA is commonly performed. It is an example where technology and basic research have been combined to deliver a tool that has been applied to a multitude of fields such as genomics, forensics, DNA/RNA aptamers optimization, and diagnostic testing.

PCR is a temperature mediated process that requires cycling between set temperatures. Single strand DNA is required for two primer sequences to bind upstream and downstream of the region to be amplified. To allow this to occur, the first step is denaturation or separation of the two strands at around 94-98° C. Primer annealing occurs around 45-55° C. and allows the thermo-stable polymerase to bind to defined regions of double stranded DNA. The next stage is elongation of the double stranded copy where the temperature is raised to the optimum temperature (around 72° C.) for the enzyme catalysis to proceed. Finally, temperature is returned to 94° C. for denaturation to single stranded DNA that allows the cycle repeat.

The thermal cycler (also known as a Thermocycler, PCR Machine or DNA Amplifier) is an apparatus used to amplify segments of DNA via the polymerase chain reaction (PCR) process. Thermal cyclers are typically provided with a thermal block with holes where tubes holding the PCR reaction mixtures can be inserted. Heat is provided through solid state heaters or infrared lamps. The cycler raises and lowers the temperature of the thermal block in discrete, preprogrammed steps.

There is a need if the field to increase the speed, and therefore the efficiency, of PCR processes. The duration of the thermocycling of a PCR process can be dependent upon several factors, including the experimentalist's requirements. Indeed, for a molecular biologist involved in sequencing large sections of a genome, amplification of large fragments would require a longer cycle time than in for more commonplace diagnostic applications, for example, to ensure high yield. The additional time required is a function of the temperature ramp time and cooling between the stages of PCR (Denaturation, primer annealing and elongation/synthesis). Shortening ramp and cooling times means more rapid transition and shorter cycling times, even appreciating for long fragments, a more substantial pause at the elongation temperature is required reflecting the polymerisation rate of the enzyme, expressed in base pairs per second (ranging from a few hundred to 1 kilobase per second). The cycle time can be shortened with more rapid enzymes or by allowing incomplete amplification of amplicons that are termed mega-primers to be completed in subsequent cycles. Though the later technique lowers the overall yield from 30 cycles it does allow slower polymerases to be utilised. More fundamental is that very few instruments on the market are available of delivering cycle times of less than 7 minutes, to full exploit rapid cycling and at a cost suitable to wide spread application.

An example of such thermocycler is the Lightcycler® that has been commercialized by Roche. The Lightcycler® can achieve heating rates of 15° C. per second with cooling rates of 10° C. per second, but commonly ramp times are significantly less than this, at around 2-5° C. per second (heating), reflecting heat delivery by Peltier elements that struggle to produce rapid heating of aluminium or ceramic blocks used to hold tubes.

Another downside of commercial real time quantitative thermal cyclers known in the art is the cost of each instrument, running into tens of thousands of dollars for rapid thermocycling. The current high cost of all PCR thermocycler platforms (real time PCR inclusive) represents a significant research cost to the experimentalist. PCR is the backbone of many molecular biological studies since its popularization by Nobel Laureate Kary Mullis and improvements to both method and instrument are always sought.

The biological components have been demonstrated to be able to run much faster than common instrumental cycle times. It would therefore be advantageous to provide an instrument which scales and lowers the cost burden such that its use becomes more widespread, while still delivering sub 10 minute reaction times for 30 cycles.

Other DNA amplifications are known in the art. One example is Loop-mediated isothermal amplification (LAMP), which involves holding a temperature (for example 65° C.) to allow Bst enzymes to perform a loop amplification using specially designed primers, to cause the formation of one massive repeating chain DNA extended polymer. Although ramping and cycling times are less of an issue, it is still desirable to provide an efficient and economical means to control the temperature of the reaction. The same can be said for any DNA amplification technique where heat needs to be applied to the reaction mixture.

Heating a reaction mixture that contains a DNA molecule is not only useful for DNA extraction techniques but is also used for other DNA-involving processes, such as cell lysis and sample sterilization.

There is therefore a need for a heating method and device for reaction mixtures containing DNA which alleviates at least some of the aforementioned drawbacks.

SUMMARY

In accordance with one aspect of the invention, there is provided a method of heating a reaction mixture containing a DNA molecule. The method includes the steps of:
  contacting the reaction mixture with nanoparticles having photo-thermal properties;
  irradiating the nanoparticles using an activation light beam activating said photo-thermal properties, such that said nanoparticles release heat sufficient to provide said heating.

Use of such a method for amplifying the DNA molecule, extracting the DNA molecule from a prokaryotic or eukaryotic entity or for sterilizing the reaction mixture is also provided.

In one variant, there is provided a method of amplifying a DNA template comprising at least one thermal cycle comprising heating a reaction mixture containing the DNA template, each of the at least one thermal cycle comprising the steps of:

contacting the reaction mixture with nanoparticles having photo-thermal properties;

irradiating the nanoparticles using an activation light beam activating said photo-thermal properties, such that said nanoparticles release heat sufficient to provide elongation and denaturation of said DNA template.

In another variant, a method of extracting a DNA molecule from a prokaryotic or eukaryotic entity is provided, comprising heating a reaction mixture containing the prokaryotic or eukaryotic entity, said heating comprising the steps of:

contacting the reaction mixture with nanoparticles having photo-thermal properties;

irradiating the nanoparticles using an activation light beam activating said photo-thermal properties, such that said nanoparticles release heat sufficient to allow extraction of the DNA molecule from the prokaryotic or eukaryotic entity.

In yet another variant there is provided a method of sanitizing a reaction mixture comprising a DNA molecule comprising heating the reaction mixture said heating comprising the steps of:

contacting the reaction mixture with nanoparticles having photo-thermal properties;

irradiating the nanoparticles using an activation light beam activating said photo-thermal properties, such that said nanoparticles release heat sufficient to sanitize the reaction mixture.

In some embodiments, the method of heating a reaction mixture containing a DNA molecule includes a step of monitoring this heating.

In one embodiment, the monitoring involves probing the nanoparticles with a probing light beam having a wavelength different than a wavelength of the activation light beam and coordinated with an absorption feature of the nanoparticles spectrally separate from the photo-thermal properties used to release heat. For example, the nanoparticles have an elongated geometry, the wavelength of the activation light beam is coordinated with a longitudinal resonance of the nanoparticles and the wavelength of the probing light beam is coordinated with a transversal resonance of the nanoparticles.

In another embodiment, the step of monitoring the heating involves contacting the reaction mixture with probing nanoparticles having an absorption feature spectrally separate from the photo-thermal properties used to release heat, and probing the nanoparticles with a probing light beam having a wavelength different than a wavelength of the activation light beam and coordinated with said absorption feature.

According to another aspect of the invention, there is provided an apparatus comprising a heating module for heating a reaction mixture containing a DNA molecule, the heating module comprising:

a thermal block for receiving the reaction mixture in contact with nanoparticles having photo-thermal properties;

a light generating assembly for irradiating the nanoparticles using an activation light beam activating said photo-thermal properties, such that said nanoparticles release heat sufficient to provide said heating.

Other features and advantages of the invention will be better understood upon reading of embodiments thereof with reference to the appended drawings

BRIEF DESCRIPTION OF THE DRAWINGS

FIGS. 1A and 1B are schematized representations of thermal block providing indirect (FIG. 1A) and direct (FIG. 1B) contact between a reaction mixture and nanoparticles heaters.

FIG. 2 is a schematized representation of an apparatus for DNA amplification according to one embodiment.

FIG. 8A is a photograph of an agarose gel and FIGS. 8B and 8C are graphic representations of the optimization of the nanoparticle content of a PCR mixture.

DESCRIPTION OF EMBODIMENTS

Figure 3:
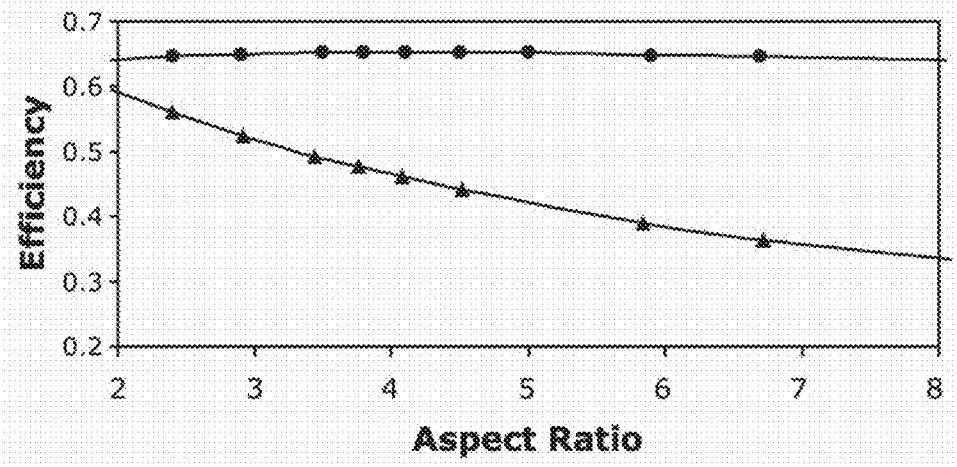
FIG. 3 is a graphic representation of the relationship observed between the diameter of the nanoparticles and their efficacy.

In accordance with one aspect of the present description, there is provided a method of heating a reaction mixture containing a DNA molecule. As will be understood from the description below, embodiments of the invention provide a heating mechanism for use in DNA applications such as DNA amplification, extraction and sterilization, through the irradiation of nanoparticles having photo-thermal properties.

Embodiments of the invention may be applied to any DNA related process where heating of a DNA template is required. It will be understood that references to DNA are also meant to encompass RNA related embodiments.

In some embodiments, the DNA process may be a DNA amplification process such as, for example, is a polymerase chain reaction (PCR) process. As mentioned above, PCR is a temperature mediated process that requires cycling between set temperatures. It therefore involves a thermal cycling of the reaction mixture through multiple heating and cooling stages. For such applications, the reaction mixture typically includes a DNA template, a primer capable of annealing to the template and a thermostable polymerase. Single strand DNA is required for two primer sequences to bind upstream and downstream of the region to be amplified. To allow this to occur, the first step of the PCR process is denaturation or separation of the two strands of the DNA template, which typically occurs around 94-98° C. Primer annealing then occurs around 45-55° C. and allows the thermo-stable polymerase to bind to defined regions of double stranded DNA. The next stage is elongation of the double stranded copy where the temperature is raised to the optimum temperature for the enzyme catalysis to proceed, topically around 72° C. Finally, temperature is returned to 94° C. for denaturation to single stranded DNA, allowing the cycle to be repeated. This cycle is repeated a number of times, typically 20 to 40 cycles.

In another embodiment, the DNA amplification may be a Loop-mediated isothermal amplification (LAMP). In LAMP, the target DNA sequence is amplified at a constant temperature, typically around 65° C. Using specially designed primers, the formation of one massive repeating chain DNA amplificons/extended polymer is obtained. LAMP alleviates the need for thermal cyclers, but still requires suitable heating capabilities and monitoring mechanisms.

Other examples of DNA amplification processes include recombinase amplification, helicase amplification, whole genome amplification or any technique using polymerase enzymes and generally requiring one or more heating steps.

In other embodiments, the heating method described herein may be used as part of a DNA extraction or isolation process. There is therefore provided a method for extracting DNA from a prokaryotic or eukaryotic entity such as a cell, virus or bacteria. Such processes may for example require performing cell lysis on a DNA sample, which may be performed by heating the cell to a predetermined temperature. In such embodiments, the expression "prokaryotic or eukaryotic entity" is understood to describe living entities as well as any DNA/RNA containing non-live entities such as phage, viruses and retroviruses.

In other embodiments, the heating method may be applied to DNA sterilization processes where heat is applied to kill bacteria in a DNA sample prior to further processing of this sample such as extraction or amplification.

Although the examples below will refer mostly to PCR, it will be readily understood, therefore that variants could be applied to other techniques where heat is to be applied to at least a portion of a DNA related process, without departing from the scope of the present invention.

The expression DNA molecule is used herein to describe a DNA molecule of interest to a process such as amplification and extraction or any other molecule part of a mixture requiring a heating step.

The expression "reaction mixture" is meant to refer to the ensemble of components required for the DNA process. In embodiments related to PCR applications, the reaction mixture may include:

The DNA template that contains the DNA target molecule to be amplified. In examples of application, the DNA template may be from genomic (human, bacterial, viral), fragmented (forensic and archaeological samples), plasmid or mitochondrial.

At least one primer. For typical PCR applications, two primers that are complementary to the 3' ends of each of the sense and anti-sense strand of the DNA target are generally provided.

A thermostable polymerase. The best known DNA polymerase used for PCR is the Taq polymerase but other types of DNA polymerase may also be used such as polymerase purified from other thermophilic microbes; computationally designed enzymes that could be modifications of either TAQ or other polymerases.

Additional reactants, including, non-exhaustively, nucleotides containing triphosphate groups such as Deoxynucleoside triphosphates, the building-blocks from which the DNA polymerase synthesizes a new DNA strand; Divalent cations, magnesium or manganese ions; and monovalent cation potassium ions.

A buffer solution which providing a suitable chemical environment for optimum activity and stability of the DNA polymerase.

Heating Mechanism and Nanoparticles

The method of heating a DNA template according to embodiments of the invention generally includes the steps of contacting the reaction mixture containing the DNA template with nanoparticles having photo-thermal properties, and irradiating the nanoparticles using an activation light beam activating these photo-thermal properties, such that the nanoparticles release heat sufficient to provide the desired heating. In effect, instead of using Peltier heaters or infrared lamps to transfer heat to the vessel containing the reaction mixture, embodiments of the invention use nanoparticles as "heaters".

The nanoparticles may be embodied by any particles of nanometric dimensions capable to release heat upon optical stimulation. Nanometer-sized particles are often defined as particles with at least one dimension below 100 nm. Particles not meeting this threshold, but still of a small enough size to exhibit properties typically associated with nanoparticles, may however still be considered within the scope of the present invention. The nanoparticles may for example be embodied by nanospheres or nanorods made of a metal such as gold, silver or the like, carbon nanotubes coated with a metal or multiwalled carbon nanotubes coated with or decorated with a metal, and the like. The metal may for example be Gold (Au), Silver (Ag), Palladium (Pd), Platinum (Pt), Iron (Fe), Copper (Cu), Aluminum (Al), Zinc (Zn) or the like. Both the dimensions and geometry of a given type of nanoparticles may have an impact on the associated heating efficiency.

The expression "photo-thermal properties" is meant to refer to the ability of a given type of nanoparticles to release heat as a result of an optical stimulation, i.e. the irradiation of these nanoparticles with a light beam having suitable optical characteristics. The photo-thermal properties may result from various chemical, geometrical or physical characteristics of the nanoparticles.

In one embodiment, the photo-thermal properties include a localized plasmon resonance at a surface of the nanoparticles, resulting in a "plasmonic heating" effect. This effect is for example observed at the surface of gold nanoparticles, spherical or having another geometry. Plasmonic heating may also be observed un gold coated or decorated multi-walled carbon nanotubes. A localized surface plasmon originates from a strong interaction between gold or silver nanoparticles and excitation light having a wavelength which resonates with the surface plasmon. Under excitation by light at the resonance wavelength a polarized charge build up at the surface of the particle leads to an oscillating dipole around the particle that exhibits an enhanced absorption and scattering cross section. The resonant wavelength is determined by the size and geometry of the nanoparticles. The energy of the resonance of the oscillating dipole is dispersed through Ohmic heating losses to the surrounding medium, raising its temperature. The energy released can be used to heat a solution rapidly where each particle becomes a heating element.

In other embodiments, the photo-thermal properties may be any process by in which energy from light is absorbed by a nanoparticle, leading to an eventual decay resulting in conversion to heat energy to the surrounding media. Nanoparticles may be mono-dispersion in solution, in direct or indirect contact with reaction components or immobilised within a polymeric material or glass.

The contact between the reaction mixture and the nanoparticles may be direct or indirect. Embodiments showing both types of contacts are shown in FIGS. 1A and 1B, respectively. In both case, a thermal block 20 where the thermal cycling of the reaction mixture occurs is shown. Referring more particularly to FIG. 1A, in the illustrated embodiment the thermal block 20 includes an inner vessel 22 in which is introduced the reaction mixture 24. The inner vessel 22 is inserted in a larger outer vessel 26. The nanoparticles 28, in this embodiment in nanofluid form, are introduced in the outer vessel 26. Both the inner and outer vessels 22 and 26 may be embodied by any appropriate structure such as tubes, capillaries and the like. An activation light beam 30 is used to irradiate the nanoparticles, which therefore release heat according to their photo-thermal properties. The heat is transferred to the inner vessel 22 and to its contents, thereby heating the reaction mixture 24. As the fluids containing the nanoparticles and the reaction mixture are kept physically separate, the contact between the nanoparticles and reaction mixture can be said to be indirect. The embodiment of FIG. 1B differs from that of FIG. 1A in that there is a single vessel 25, in which the nanoparticles 28 are provided in solution with the reaction mixture 24. In this case, the contact can be said to be direct. In other variants, indirect contact could also be defined as an emulsion of a modified nanofluid and water. The expression "contacting the reaction mixture with nanoparticles" is understood to refer to providing either direct contact, indirect contact or both at the same time.

In some embodiments, in particular where the nanoparticles are in direct contact with the reaction mixture, care should be taken so that the nanoparticles do not interfere with the DNA related process to be performed. For example, in PCR embodiments, the polymerase may bind to the surface of the nanoparticles, blocking positive active site by association with a negatively charge particle surface, and therefore inhibiting the polymerase from performing its function during the DNA amplification process. In accordance with some embodiments, therefore, the nanoparticles have a surface modification by a chemical compound such as Polyethylene glycol (PEG) or any other chemical equivalent that prevents the inhibition of a positive active site of polymerase class enzymes.

In one example, 840 pM of uncapped gold nanorods is mixed vigorously with an aqueous thiol PEG 5000 MW solutions (1 mg/ml) in equal volumes and incubated at 30° C. for 2 hours (elevated temperature decreases reaction time for formation of Au-S-PEG complex). The mixture containing the nanorods is centrifuged down at 13,000 RPM, in order to remove the supernatant. The nanorods are resuspended in MilliQ water using a vortex and afterwards centrifuge down again to form a highly coloured pellet, with a final resuspension in DNase/RNase free water.

One advantage of the surface modification described above is that the resulting nanoparticles can be used as generic heaters independently of the type of polymerase, size of the template or template type. Inhibition prevention will apply to any application, avoiding the additional complication of limiting the application of the method to specific polymerase types.

In various embodiments, the dimensions of the nanoparticles may be selected in view of optimizing the resulting heating efficiency. Referring to FIG. 3, there is shown a graph of the heating efficiency of gold nanorods with respect to their aspect ratio (defined as the longitudinal axis divided by the diameter in nanometers), for nanorods having a diameter of 10 nm and 25 nm. In this comparison it can be seen that the nanorods of 10 nm of diameter provide a greater heating efficiency.

Figure 4:
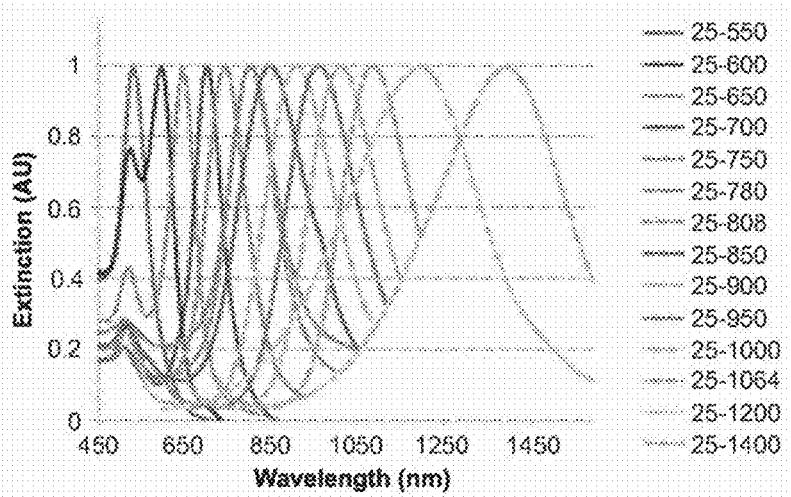
FIG. 4 is a graphic representation of the variation of extinction (AU) in view of the wavelength (nm) used.

In various embodiments, other factors can be controlled to improve heating efficiency of the method. As predicted by the Beer-Lambert law, a higher rod concentration and shorter path-length will maximize the absorbance of the activation light beam. By way of example, to study the optimization of the heating process, data was calculated from commercially available nanorod solution from Nanopartz (tradename) with no capping ligand. The resonance spectra for the various nanoparticles studied is shown in FIG. 4. Referring to Table 1, data showing the optimization of the resonance of the nanoparticles, path length and concentration to achieve maximum absorbance is presented. For each nanoparticle model considered, designated by part number, Table 1 lists the wavelength if the surface plasmon resonance (SPR), the maximum concentration of nanoparticles in the solution, and the converted power for an optical path length of 0.5 cm.

TABLE 1

Optimization of the resonance of the nanoparticles, path length and concentration

| Part Number | SPR (nm) | Maximum Concentration (pM) | Stock Concentration (%) | Converted Power for 0.5 cm Optical Path Length | |
|---|---|---|---|---|---|
| | | | | Maximum Concentration (%) | 26.3 pM (%) |
| A11-60 | 536 | 6.58 | 61.5 | 14.5 | 45.5 |
| A12-10-808 | 808 | 57.7 | 65.3 | 95.4 | 95.4 |
| A12N-25-1400 | 1400 | 3.70 | 29.0 | 42.4 | 42.4 |
| A12N-25-1064 | 1064 | 5.64 | 36.4 | 53.2 | 53.2 |
| A12-25-980 | 980 | 6.48 | 39.0 | 57.0 | 57.0 |
| A12-25-850 | 850 | 8.38 | 44.2 | 64.5 | 64.5 |

TABLE 1-continued

Optimization of the resonance of the nanoparticles, path length and concentration

| Part Number | SPR (nm) | Maximum Concentration (pM) | Stock Concentration (%) | Maximum Concentration (%) | 26.3 pM (%) |
|---|---|---|---|---|---|
| A12-25-808 | 808 | 9.28 | 46.1 | 67.5 | 67.5 |
| A12-40-650 | 650 | 6.10 | 36.0 | 52.6 | 52.6 |
| A12-40-700 | 700 | 3.22 | 21.7 | 31.7 | 31.7 |

As seen from Table 1, heating efficiency can be impacted by selection of the nanoparticles and concentration parameter. Also, if 95% absorbance at 808 nm is achieved, path length can be reduced significantly. Concentration used was increased from 26.3 pM to more than 800 pM, which allows a reduced path length to be applied. Under the Beer-Lambert law absorbance increases as concentration increases, allowing a short path length through a solution to be used with respect to achieving the same heating rate as for a low concentration of particles. Furthermore, it allows miniaturisation of sample volume. This allows the method to translate to bulk heating of water within micro channels. Using the scaling factor of 840 pM/2 pM, this indicates how much it is possible to increase nanoparticle concentration, by 32.3 times for example. This also means that the path length can be reduced by the same scaling. Shorter path lengths are needed to achieve the same absorbance effectively. The path length was reduced to 0.154 mm which is of the order of the height of a microfluidic channel. The method is therefore applicable to microfluidic chips such as the Fluidigm (tradename) system for digital PCR.

Apparatus

Referring to FIG. 2, an apparatus 32 for performing DNA extraction according to one embodiment is schematically illustrated.

The apparatus first includes a thermal block 20 for receiving the reaction mixture in contact with nanoparticles having photo-thermal properties. The thermal block may be embodied by any container, chamber, assembly, or other structure adapted to receive the reaction mixture and nanoparticles and provide optical access thereto. As mentioned above with respect to FIGS. 1A and 1B, the thermal block may be configures to provide indirect or direct contact between the reaction mixture and nanoparticles. In the illustrated embodiment, by way of example only, the thermal block 20 is embodied by a glass capillary sized to receive from 25 to 40 μl of the solution containing the reaction mixture and nanoparticles. A thermocouple 21 may optionally be used to measure the temperature change in the vessel containing the nanoparticles.

The apparatus 32 further includes a light source 34 for irradiating the nanoparticles using an activation light beam 30 activating their photo-thermal properties, such that the nanoparticles release heat sufficient to provide the desired heating. In one embodiment, the light source 34 may be embodied by a laser or LED (light-emitting diode) generating light at a wavelength coordinated with the photo-thermal properties of the nanoparticles. The light source may be part of a light generating assembly allowing a control of optical parameters of the activation light beam such as the wavelength, optical power, duty cycle in embodiments where the light beam is pulsed, spot size, etc. Various means of adjusting such parameters are well known in the art and need not be described here. By way of example, in the illustrated embodiment, the light source 34 generates an activation light beam 30 having a wavelength of 532 nm resonant with a plasmon resonance of gold nanorods, and a coil-based shutter 36 is provided in a path of the activation light beam 30 before it reaches the thermal block 20. The shutter 36 may for example be used to periodically block the activation light beam 30 to reduce the average light power reaching the thermal block 20. In other embodiments a different mechanism may be used to control the light power such as for example direct modulation of a laser or LED light source (such as TTL modulation), use of a modulating device such as an intensity of phase modulator, etc. Of course, one skilled in the art will readily understand that a number of additional optical components may be provided in the apparatus 32 depending on particular design considerations, such as lenses, mirrors, filters, polarisers, amplifiers, and the like without departing from the scope of the present description.

The optical parameters of the activation light beam 30 are preferably determined and controlled in view of the photo-thermal properties of the nanoparticles. By way of example, in one embodiment the necessary light power to achieve a desired temperature through release of heat from the nanoparticles can be calculated from theoretical considerations related to plasmonic heating. The heat released by a given nanoparticle can be evaluated using Equation (1) below, taking for example a sphere-shaped nanoparticle, also referred to as a nanosphere. To briefly summarize equation (1), $\Delta T_{max}$ is the steady-state surface temperature of the nanosphere relative to the external temperature at distances much greater than the dimensions of the nanosphere, $\omega$ is the harmonic frequency of the incident radiation (related to the light wavelength), R is the nanosphere radius, $I_0$ is the intensity of the incident radiation, c is the speed of light in vacuum, $k_0$ is the thermal conductivity of the external solution, $\in_0$ is the relative complex permittivity of the external solution, $\mu_0$ is the relative magnetic permeability of the external solution, and $\in_m$ is the relative complex permittivity of the nanosphere:

$$\Delta T_{max} = \frac{\omega R^2 I_0}{3ck_0\sqrt{\varepsilon_0\mu_0}} \left|\frac{3\varepsilon_0}{2\varepsilon_0 + \varepsilon_m}\right|^2 \text{Im}[\varepsilon_m] \quad (1)$$

Assuming that the incident laser beam has a flat-top profile and that the reaction mixture is non-absorbing at the wavelength of the activation light beam, the above relation can be inverted in order to find the required laser power for a given surface temperature, where P is the incident laser power and d is the laser spot diameter (equation 2).

$$P = \frac{I_0\pi d^2}{4} = \frac{3ck_0\sqrt{\varepsilon_0\mu_0}\,\Delta T_{max}}{4\omega R^2}\left|\frac{2\varepsilon_0 + \varepsilon_m}{3\varepsilon_0}\right|^2 \frac{\pi d^2}{\text{Im}[\varepsilon_m]} \quad (2)$$

Time of exposure can also be varied to control the raising of the temperature of the reaction mixture. As one skilled in the art will readily understand, the intensity of the activation light beam and the time of exposure are two parameters which can easily be controlled in conjunction to control the rate at which energy is transferred to the nanoparticles and, consequently, the temperature of the reaction mixture.

The wavelength of the activation light beam is another optical property which can be determined and controlled in view of the photo-thermal properties of the nanoparticles. As mentioned above, in the case of plasmonic heating, the release of heat by the nanoparticles results from their stimulation using light having a wavelength matching the localized plasmon resonance at the surface of the nanoparticles. Furthermore, in embodiments using light-induced plasmonic heating a wavelength selectable characteristic can be conferred upon the process of heating. Within the bandwidth of excitation, heating of a solution can be turned on and off readily, accentuated by greater dispersion of heat from the solution simply by the presence of nanoparticles within the reaction mixture that should, in effective combination with a cooling system, lead to rapid temperature transition, hence shorter PCR cycle times. Carbon nanotubes, in contrast, absorb light in to energy levels pertaining to both the semi-conducting and, if metallic elements are present, energy levels pertaining to the presence of the metals. The broad absorbance of carbon nanotubes can be explained by many additional transitions possible from the ground state over the visible and into the near infra red for the promotion of an electron. The wavelength of the absorbance pertains to the difference in energy between the ground state and the excited state. In any case, by choosing, and optionally varying, the wavelength of the excitation light beam to match a resonance or transition of the absorption spectrum of the nanoparticles, control of the heat released through the photo-thermal properties may be achieved and/or optimized.

Still referring to FIG. 2, the apparatus 32 may include any other component typical of DNA amplification, extraction or sterilization devices. For example, in the illustrated example, directed to PCR applications requiring thermocycling, a fan 38 is provided in proximity to the thermal block 20 and can be activated to accelerate the cooling of the reaction mixture during the cooling phases of the thermocycling. A fan controller 40 preferably allows a control of the activation of the fan 38. Overall control of the apparatus can be managed through any appropriate device or combination of devices. In the illustrated embodiment, by way of example only, a computer 42 provides electrical control signals to the light source 34 and fan controller 40 through an appropriate electrical interface 44, for example an FPGA circuit board.

Real-Time Monitoring

In accordance with one aspect of the invention, the method may include an additional step of optically monitoring, in real time, the temperature change resulting from heating a reaction mixture according to embodiments of the invention.

Optical properties of nanoparticles can provide a useful spectroscopic approach for real time monitoring of the reaction. A change in the temperature of the environment of the nanoparticles also affects the local dielectric constant, which leads in a drift of the optical properties of the nanoparticles. By using a probe light beam having a wavelength coordinated with a different absorption feature than the one used for heat release, this drift can be measured, therefore monitoring the corresponding temperature change, by interrogating the nanoparticle resonance with the probe light beam and monitoring a change in either the scattering or absorbance at a fixed probe wavelength.

Figure 5A:
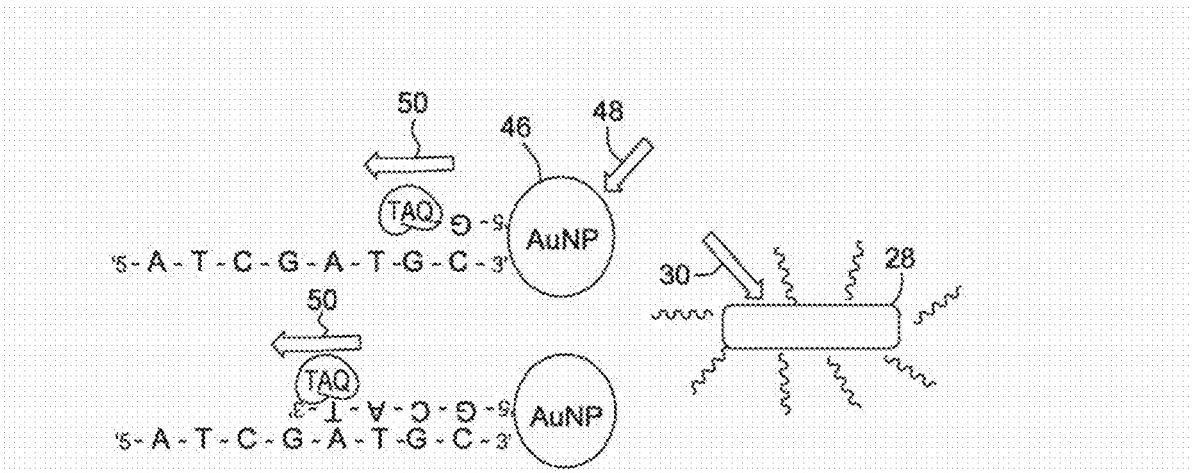
FIG. 5A is a schematized representation of the use of probe nanoparticles for temperature monitoring.

In some embodiments, probing nanoparticles having an absorption feature at a wavelength different from the wavelength used to activate the photo-thermal properties of the nanoparticles used for heating can be put in contact with the reaction mixture. Referring to FIG. 5A, there is shown a schematized illustration of the resulting monitoring principle. In the illustrated example, the heating nanoparticles 28 are embodied by nanorods having a localized plasmon resonance as explained above, releasing heat when irradiated with the activation light beam 30 having a wavelength corresponding to that resonance, for example at about 532 nm or 808 nm when considering gold nanorods (bother resonant frequencies can be changed by particle dimension and the dielectric constant of the medium or surface ligands around them). Probe nanoparticles 46, here embodied by gold nanospheres, are put in direct contact with the reaction mixture. In the illustrated example of FIG. 5A, the gold nanosphere are shown as covalently attached to the primers and DNA template. Covalent attachment of primers would result in a great local dielectric shift at the surface of the gold nanoparticles as amplicons would be confined in close proximity to the gold. The plasmonic field propagates approximate tens of nanometers from the surface and changes at the surface more greatly affect the plasmonic shift measured as a red shift of the plasmonic peak. The gold nanospheres used for sensing production of amplicons would have a resonance, blue shifted from the resonance of the nanorods used for heating purposes. The probe nanoparticles are irradiated with a monitoring light beam 48 having a wavelength within the resonance of the gold nanospheres. Return light 50 resulting from the interaction of the monitoring light beam with the monitoring nanoparticles is detected and analysed. The intensity of the return light varies according to the degree of absorption of the monitoring light beam 48 by the gold nanospheres. As the temperature varies, the resonance of the monitoring nanoparticles shifts, and the wavelength of the monitoring light beam falls in and out of resonance, changing the degree at which the monitoring light beam is absorbed.

In one example, gold probe nanoparticles are covalently linked to the primers through a thiol linkage added to the 5' end of the primer and linked to the gold through the sulphur atom. As PCR proceeds through annealing, elongation and denaturation, the dielectric constant around the nanoparticle will change dynamically, first with the binding of single strand DNA to primers, then with elongation of the single strand to double strand and finally again with removal of double stranded copy from particle surface. The stage of the reaction could be monitored similarly to that of SYBR fluorescence during real time PCR. Using a separate plasmonic resonance for the probe and heating nanoparticle species, the heating nanoparticles will not interfere with measurement at the probe wavelength relative to the resonance of the probe nanoparticles. In some embodiments, the probe nanoparticles may have a spherical geometry and be assess by illumination with white light and measuring the absorbance using a CCD with a bandpass filter centered around the resonance peak. The heating nanoparticle species may be gold nanorods as nanorods have greater extinction coefficients than spherical particles and will produce more heating power per unit of laser power incident upon the nanoparticles.

The wavelength used to initiate plasmon resonance is dependent upon the geometry of the particle. For example, a 532 nm source as used and exemplified herein may not represent an optimum combination of laser wavelength and particle for some applications and can be modified depending on the particles and conditions used. The high cost of lasers in this spectral range would impact upon the uptake of this method, and light source costs can be significantly reduced by using a less expansive laser system or a LED, and choosing and designing the nanoparticles accordingly. Heat transfer can be improved by using a particle with a large absorption cross-section and hence great extinction co-efficient. One combination as described herein consists of a 1 W laser diode at 808 nm and gold nanorods with an absorptivity of 5.96×10$^{12}$M-1 cm-1 at the same wavelength. This takes advantage of a significant cost reduction and increase in efficiency of heat generation by nanoparticles and offers the potential for multiple nanoparticle systems that could be easily multiplexed. In such a system, heating could be accomplished by a class of nanoparticles with a superior absorption cross-section and another class(es) of nanoparticles modified using primers could be used as the probe for the reaction, demonstrating binding of new amplicon fragments upon the particle surface by changing the resonant absorbance and spectral position. If a fluorescence system is required, the additional benefit of changing wavelengths would be to enable the combination with conventional quantitative PCR methods using intercalating fluorescence dyes such as SYBR green. The laser will be significantly red-shifted off the fluorescence limiting interference and eliminating issues of dye photobleaching expected with operating a 532 nm laser at almost 3 W optical power.

In other variants, the same nanoparticles used to release heat may be used for optical monitoring as well. For example, in the case of nanorods, the elongated geometry of the nanoparticles results in two distinct surface plasmon resonances, respectively aligned with the longitudinal and transversal axes of the nanorod. These two resonances interact with light at very distinct wavelengths—for example, the longitudinal resonance of gold nanorods absorbs light around 808 nm, whereas the transverse resonance absorbs light around 560 nm, and can be used as the monitoring resonance.

Figure 5B:
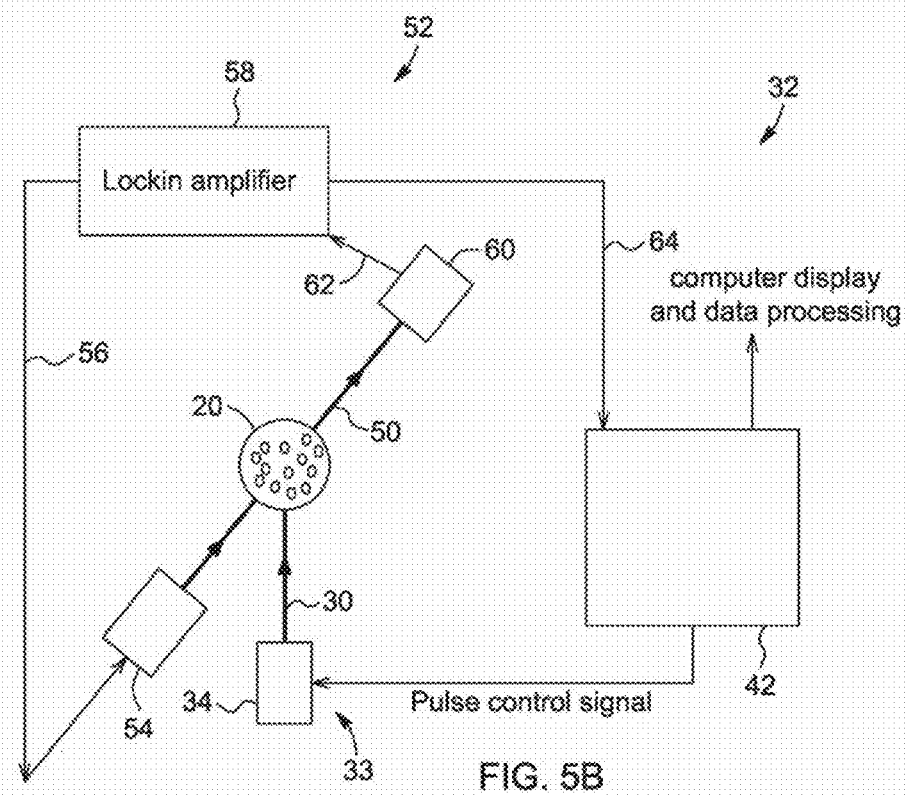
FIG. 5B is a diagram of an apparatus for DNA-related applications comprising a heating module and a monitoring assembly according to one embodiment.

With reference to FIG. 5B, there is shown a schematized representation of an apparatus 32 for DNA amplification, extraction or sterilization which includes both a heating module 33 and a monitoring assembly 52. As explained above, the heating module 33 includes a thermal block 20 for receiving the reaction mixture in contact with nanoparticles having photo-thermal properties, and a light generating assembly such as heating laser 34 for irradiating the nanoparticles using an activation light beam 30 such that the nanoparticles release heat sufficient for the application-related heating purpose. The nanoparticles having photo-thermal properties may have a second resonance that can be used for probing, or different probe nanoparticles may be put in contact with the reaction mixture in the thermal block 20 to provide monitoring capabilities. The monitoring assembly 52 includes a probing light source 54 for irradiating the thermal block 20 with a probing light beam having a wavelength different than a wavelength of the activation light beam, and coordinated either with the second resonance of the heating nanoparticles or with a resonance of the probe nanoparticles, if provided. In the illustrate embodiment, the probing light beam 30 outputted by the probing light source 54 is modulated by a pulsing signal 56 from a locking-amplifier 58. The light of the probing light beam 30 is absorbed by the nanoparticles, changing the transmission of light through the thermal block 20. The corresponding light outputted from the thermal block 20, herein referred to broadly as "return light" 50, is measured by a detector 60, such as for example a photodiode. The photodiode signal 62 is passed through a pre-amp and the locking amplifier 58 performs a comparator function to eliminate signal not related to the modulation frequency.

The photodiode signal 62 may also be compared to a reference photodiode (not shown) that accounts for laser power fluctuations. The signal from this reference photodiode is used to normalise the signal from the sensing photodiode and the result is transmitted as an analog monitoring signal 64 to the controller 42.

As amplicons are formed the resonance moves changing the absorbance and moving the plasmon relative to the probe wavelength. Hence the reaction can be monitored.

The real-time monitoring method described herein presents several potential applications, and, apart from sequencing, extend to ultra fast diagnostic PCR testing utilising the rapid heat transfer enabled by diffuse nanoscale heaters. It also removes the requirement for capillary electrophoresis as a readout methodology. In addition, a reduction in total volume from microliter volumes used in commercial thermocyclers to nanoliter or picoliter volumes common to chip-level PCR approaches are also encompassed.

EXAMPLES AND EXPERIMENTAL RESULTS

Example 1

Referring to FIGS. 1 A, 2, 6 and 7, the results of a first demonstration of the heating principle described above are shown. In this example, an apparatus such as illustrated in FIG. 2 was used, and the nanoparticles were put in indirect contact with the reaction mixture, such as shown in FIG. 1 A. The PCR reaction mixture was placed within a 0.5 ml tube and covered with 150 µl of mineral oil to prevent evaporation. The reaction mixture contained: Phusion polymerase (0.02 units/µl), 1×PCR buffer--, nucleotides (10 mM), forward (5'-AACCAGCCCGACTCCTTTG-3') (SEQ ID NO:1) and reverse (5'-CAGGGGCCAAGTAGAG-CATC-3') (SEQ ID NO:2) primers, bovine serum albumin (10 µg/µl), BHEX plasmid containing the human androgen receptor cDNA (103 ng) and dionized water. Final volume was 25 µl. The glass reaction tube was immersed in a 300 µl volume of nanoparticles embodied by gold nanospheres within a 1.5 ml tube and sealed with parafilm.

An activation light beam from a Melles Griot continuous wave laser at a wavelength of 532 nm and power of 2.7 W was used to irradiate the double tube containing the nanoparticles and reaction mixture. An optical shutter and cooling fan were operated through an Arduino microcontroller and Labview interface; a 1K thermocouple was inserted into the reaction mixture to record temperature via the microcontroller. The graphical interface allowed set temperatures for each stage of the reaction to be defined as well as the period of time for which each temperature was to be maintained. Communication between the computer and micro-controller was via a USB link. Defined temperatures and times allowed a negative feedback control mechanism to be instigated where the fan and optical shutter could be actuated to dynamically alter pulsed excitation of plasmons dependent upon temperature required and stage of the reaction cycle.

Figure 6:
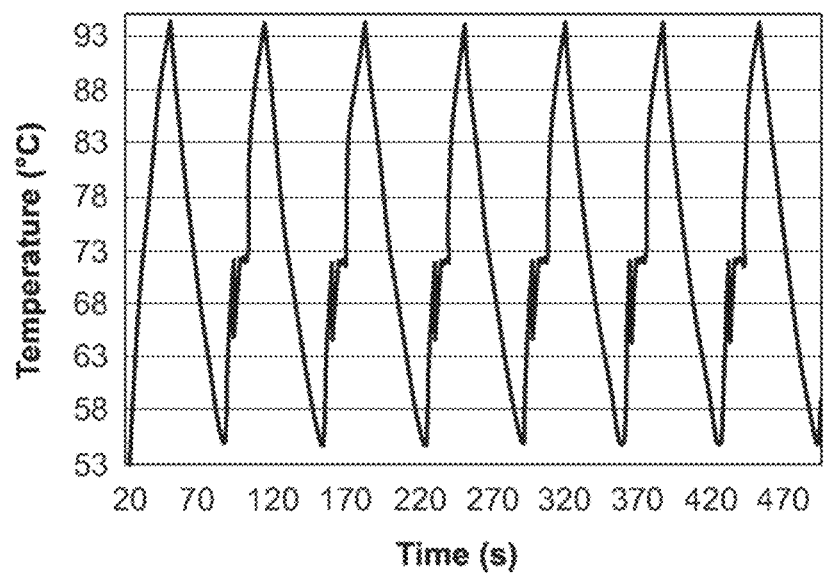
FIG. 6 illustrates a thermal cycling demonstration graphic.

Stability of temperature was demonstrated when using plasmonic heating. Annealing (55.18+/−0.09° C.), elongation (72.03+/−0.13) and denaturing temperatures (94.09+/−0.1° C.) demonstrated accuracies of 0.1° C. overall. Elongation temperatures are defined for the point where the plateau temperature is reached. FIG. 6 demonstrates the thermocycling achieved with plasmonic heating; total reaction time for this experiment was 45 minutes. A reaction was established following the thermal trace in FIG. 6 where DNA was denatured at 94° C. (5 seconds), annealed at 55°

Figure 7:
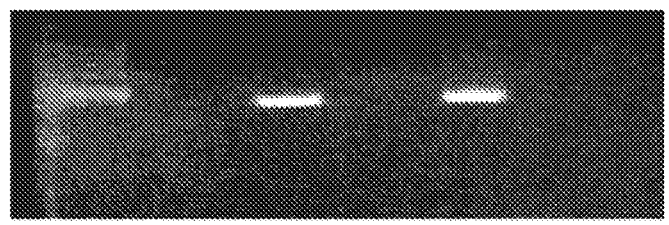
FIG. 7 is a photograph of a 1.5% agarose gel demonstrating the formation of product through use of a plasmonic thermocycler.

C. (20 seconds) and extension or elongation phase occurred at 72° C. (45 seconds). The resulting product was separated on a 1.5% agarose gel by electrophoresis (FIG. 7). Lane 2 contains a positive control produced by a commercial Eppendorf Master thermocycler, lane 3 the negative control and lane 4 the product from the plasmonic thermocycler. Products were visualized using ethidium bromide and UV gel station, the size marker used was φX174 DNA-HaeIII digest (lane 1).

This example demonstrates that the indirect-contact method can be used to provide sufficient heating for some target applications. It is to be noted that such embodiments may have the drawback of requiring a large volume of nanoparticles to heat a small volume of PCR mixture, and may be an impractical method for potential miniaturisation.

Example 2

Referring to FIGS. 8 to 11, a second example is provided using a direct contact approach, i.e. directly mixing the nanoparticles with the reaction mixture such as for example shown in FIG. 1B. With a particular view to potential PCR applications, the impact of a number of factors was assessed, such as whether the concentration of nanoparticles is sufficient for heating to occur and at what concentration do gold nanoparticles of 60 nm diameter inhibit the polymerase.

First, the potential inhibition of the PCR reaction with gold nanoparticles was investigated in combination with a PCR additive such as bovine serum albumin (BSA) to prevent polymerase adhering to the nanoparticles. It is likely that the mechanism for inactivation of the polymerase involves the positively charged active site adsorbing to the surface through electrostatic interactions with the negatively charged citrate capped nanoparticles. This would effectively exclude the binding of single-stranded DNA. The physical adhesion to the surface of BSA should create a coating layer, allowing the polymerase to remain free in solution.

Using a dilution series from the stock gold nanoparticle solution (26.3 pM), water was replaced with increasing volumes of gold nanoparticles in aqueous solution to yield concentrations ranging from 4.4 pM to 17.9 pM within a PCR mixture. Each reaction has an increasing quantity of gold nanoparticles. Reactions were performed upon an Eppendorf thermocycler and at 4.4 pM no inhibition of the reaction was observed as shown in FIG. 8A. In addition, FIG. 8B shows a measurement of the localised surface plasmon absorbance at the concentration of 4.4 pM to demonstrate that the resonance wavelength is unaffected by incorporation into the PCR mixture, as the resonance is still at 532 nm. On the gel it is clear that the control product in lane 2 matches that of the reaction with 4.4 pM of nanoparticles as an addition to the mixture. Subsequent experimentation demonstrated that the addition of 1.5 ml of 10 ng/ml BSA to the mixture also allowed a greater quantity of nanoparticles to be added; up to 6.6 pM could be used.

The direct contact heating approach did not initially yield a product from the thermocycling or in repeat experiments where low concentrations of nanoparticles and longer reaction cycles were applied. To resolve the source of the reaction inhibition an exclusion study was performed based on three hypotheses. The first hypothesis considered that a 532 nm laser used to excite plasmons also presents the potential for 2 photon absorbance by thymine residues and the formation of cyclobutyl pyrimidine commonly known as a fused base pair that would prevent effective denaturation of double strand DNA and polymerase action. The mechanism is through the absorbance of two photons of longer wavelength hence lower energy equal to the energy of a single UV photon (~250-260 nm). The second hypothesis was a 2 photon absorbance by aromatic amino acids (tyrosine, tryptophan, phenylalanine) in the Phusion polymerase. The mechanism in this event would be the generation of free radical oxygen leading to protein denaturation through excitation of the triplet state commonly associated with aromatic amino acid fluorescence, but a consequence of triplet state occupancy is the potential generation of highly reactive singlet oxygen. A third hypothesis can be made that excludes the potential of singlet oxygen but considers two potential nanoparticle related effects. A concern was that polymerases, as with other enzymes, are known to interact with gold nanoparticles by electrostatic adsorption to the particle surface, this would effectively block the active site preventing DNA polymerisation. The second potential effect was denaturation of proteins via nanoparticle heating as has been observed for albumin. This would present a framework for investigating the reaction failing in both rapid and conventional cycling using the contact plasmonic PCR method.

To investigate these three hypotheses a set of reactions was established using both the plasmonic thermocycler and a conventional commercial thermocycler. The PCR mixture, gold concentration, water and enzyme quantities are identical to earlier experiments for contact PCR, where the gold concentration was 4.4 pM.

TABLE 2

Thermocycling runs used to determine the cause of PCR inhibition

| Reaction | DNA | Phusion | Addition | Lane | Product |
| --- | --- | --- | --- | --- | --- |
| 1M | Yes | Yes | N/A | 1 | Yes |
| 1L | Yes | Yes | N/A | 6 | No |
| 2M | No | Yes | DNA | 2 | Yes |
| 2L | No | Yes | DNA | 3 | No |
| 3M | Yes | No | Phusion | 5 | Yes |
| 3L | Yes | No | Phusion | 4 | Yes |

Table 2 shows the reactions established. 1M and 1L are PCR reactions run for 30 cycles in either the conventional PCR instrument (Eppendorf Mastercycler or M) or the plasmonic thermocycler (L). 2M and 2L are run for 15 cycles in either instrument without DNA present to assess the effect of heat treatment or laser irradiation upon the Phusion enzyme respectively prior to a full 30 cycle run in the Mastercycler to see if the reaction will proceed to formation of product. 3M and 3L also are treated for 15 cycles in the Mastercycler and plasmonic thermocycler separately, but with DNA present in the mixture to assess potential of damage to DNA prior to conventional amplification. In all cases, if the component of the reaction that is present is damaged, then it will become evident as no product will be formed by the conventional amplification in the Mastercycler following the treatment in the plasmonic thermocycler. The 30 cycle reaction conducted after plasmonic thermocycler pre-treatment was under the following conditions: 98° C. for 30 s hot start, 96° C. for 45 s, 55° C. for 45 s and 72° C. for 45 s. The laser was operated at 2.7 W optical power as before. The temperature protocol was used consistently between each instrument with respect to cycling.

Figure 9:
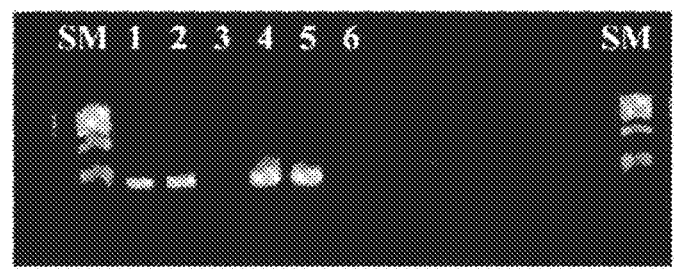
FIG. 9 is a photograph of a gel using pre-treatment to determine whether damage is occurring to either DNA or enzyme components of the PCR reaction mixture, wherein SM denotes size markers.

The results are indicated in Table 2 and in the gel image in FIG. 9. 1M provided the positive control for the experiment and produced product, confirming that the master mixture was made competently. 1L was the negative control where no template DNA was present and it produced no product, confirming no contamination of the master mixture. 2M produced PCR product, removing the possibility of simple heat-related denaturation of Phusion, whereas 2L produced no product suggesting possible laser damage of the enzyme or some other form of enzyme deactivation. 3M and 3L did not initially have any enzyme present during their heat and laser pre-treatment respectively, but primer and template DNA were present and had enzyme added after. Both reactions were finished in the conventional thermocycler and produced products. This indicated that no DNA damage resulted from laser irradiation in the presence of gold nanoparticles.

The second possible conclusion is that the enzyme had been deactivated through denaturation or inactivation. As part of the hypothesis for this experiment a photochemical route to generating free radicals was considered. It should also be noted that gold nanoparticles have the potential to form oxygen free radicals, but no evidence for DNA damage can be demonstrated for the concentration of nanoparticles in the reaction mixture as seen by the successful product formed from reaction 3L. It was concluded that the source of reaction failure was linked to the enzyme; the exact method of inhibition was still unclear as experiments to quantify singlet oxygen using trans-1-(2'-methoxyvinyl) pyrene proved inconclusive.

Figure 10:
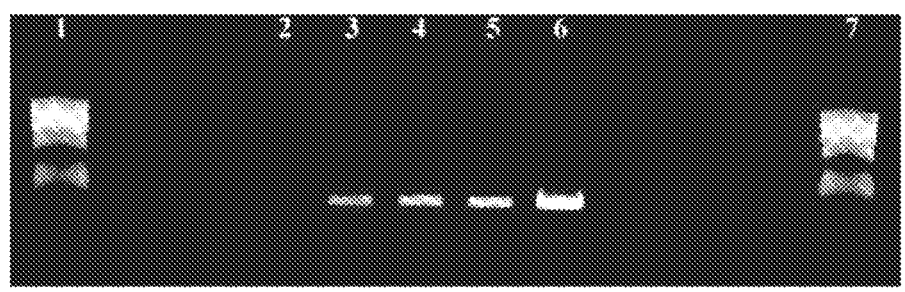
FIG. 10 is a photograph of PCR products obtained by plasmonic PCR with nanoparticles in the PCR mixture, wherein lane 1: size markers; lane 2: negative control; lane 3: plasmonic PCR product (10 µl loading); lane 4: plasmonic PCR product (20 µl loading); lane 5: plasmonic PCR product (20 µl loading); lane 6: positive control (conventional PCR); and lane 7: size markers.

A simpler explanation was considered than either of the above three hypotheses. The presence of the thermocouple in the reaction mixture has been shown to inhibit polymerases previously, and was solved by the addition of PEG-8000 to the reaction mixture. The opportunity for volume reduction well in advance of current picoliter systems and the rapid heat exchange over small distances leading to greater reduction in reaction times necessitated a trial of this simple solution. The addition of PEG-8000 (0.9% w/v) allowed the demonstration of the contact plasmonic PCR reaction with nanoparticles within the reaction mixture. In addition, a lower denaturation temperature of 90° C. was required as it appears that the nanoparticles may aid denaturation at lower temperatures. FIG. 10 contains the electrophoresis image of the agarose gel. Lanes 3-5 contain products amplified by plasmonic PCR, lane 2 provides the negative control and lane 6 is the positive control using a commercial PCR instrument.

All reactions in this example were performed using taq polymerase. Temperature conditions were 90° C. (30 s), 55° C. (30 s) and 72° C. (30 s) until the final 5 cycles where annealing and elongation times were increased to 45 seconds. This represents the first demonstration of a PCR reaction driven by nanoparticle plasmonic heaters in direct contact with DNA and the polymerase.

Figure 11:
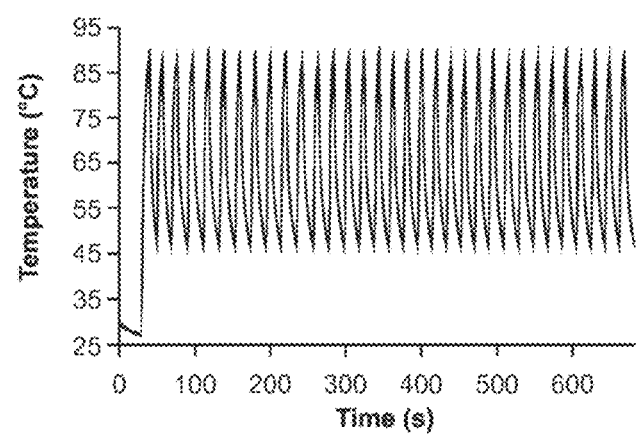
FIG. 11 is a graphic representation of a thermal trace of 30 rapid cycles.
Figure 12:
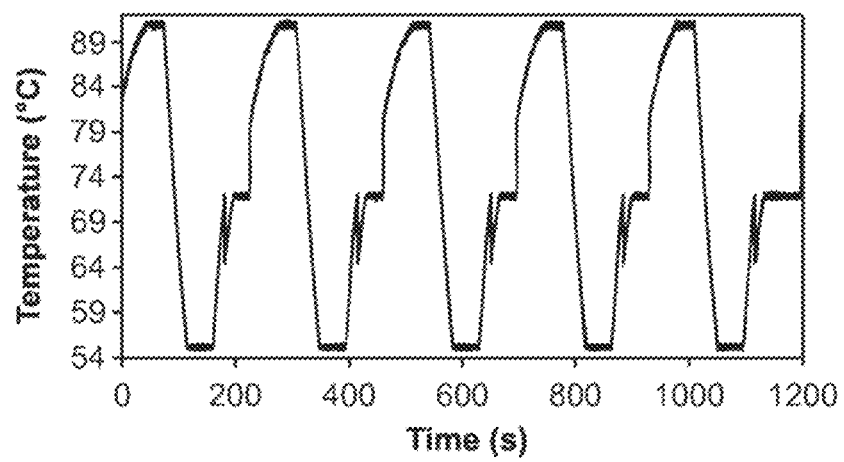
FIG. 12 is a graphic representation of a contact PCR experiment trace cycling between 91° C. (denaturation), 55° C. (annealing), and 72° C. (elongation), wherein the spike present when transitioning from 55° C. to 72° C. and the jumps from 72° C. to around 80° C. are not physical and are due to problems with the instrument readout.

Careful analysis of the thermocycler's temperature control was performed to provide a comparison to commercial systems and also to characterise the regulation of temperature. In order to determine maximum heating and cooling rates, a run was performed whereby the solution temperature was rapidly cycled between 45° C. and 90° C. (FIG. 11). The temperature range mirrors the same denaturing and annealing temperatures as performed by Wheeler et al. (2011, Analyst, 136: 3707-3712) and their rapid cycling approach. Data were also acquired from a contact PCR experiment for the purpose of ascertaining temperature stability (FIG. 12).

Figure 13:
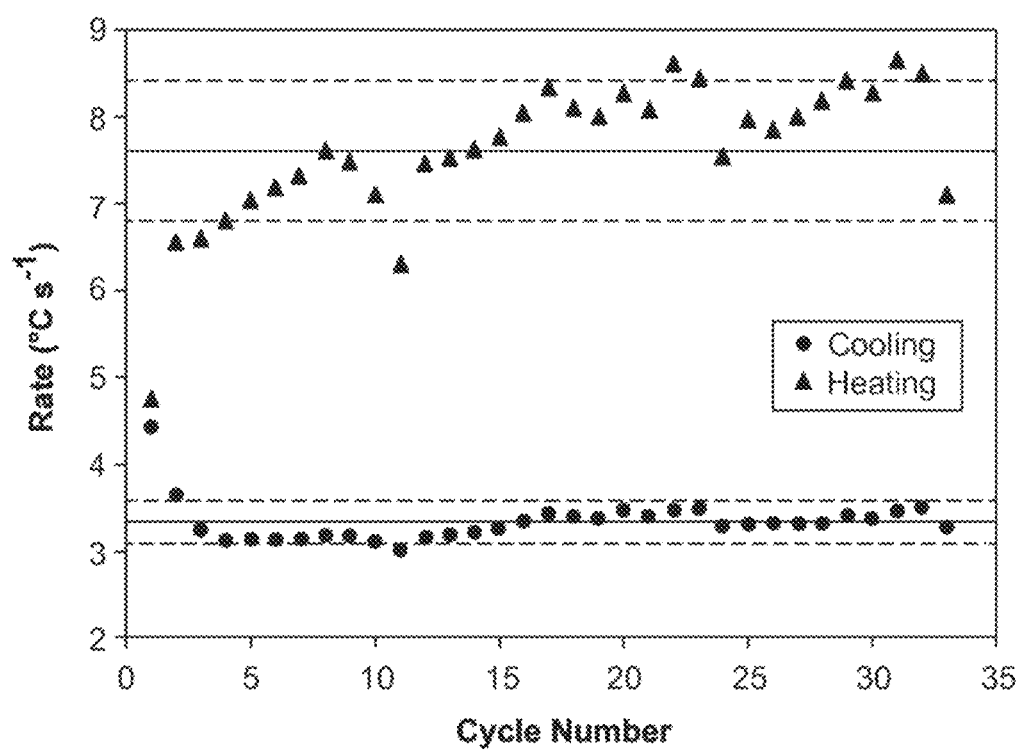
FIG. 13 illustrates the heating and cooling rates obtained from rapid temperature cycling, wherein solid lines denote average values and dashed lines are located one (sample) standard deviation away from averages.

Using the rapid cycling data, heating and cooling rates were calculated by measuring the difference between successive temperature maxima and minima, then dividing by the time interval between them. The average rates and sample standard deviations were obtained. FIG. 13 and Table 3 detail the results.

TABLE 3

Results of temperature data analysis where standard deviation is a measure of precision

| Temperature change rates | |
|---|---|
| Heating | 7.62 ± 0.81° C. s$^{-1}$ |
| Cooling | 3.33 ± 0.24° C. s$^{-1}$ |
| Temperature stability | |
| Denaturation at 91° C. | 90.87 ± 0.17° C. |
| Annealing at 55° C. | 55.10 ± 0.16° C. |
| Elongation at 72° C. | 71.92 ± 0.15° C. |

The heating and cooling rates obtained are 7.62±0.81° C./second and 3.33±0.24° C./second, respectively. FIGS. 1A to 14C indicate that the heating and cooling rates start to stabilise after 10 cycles. Heating rates initially increase whereas cooling rates decrease. This could be due to the Eppendorf plastic tube gradually heating up until it reaches a stable temperature. Conversely, one of the fan effects during cooling would be to create a velocity distribution of the air that is repeatable from cycle to cycle, leading to a smaller spread of the cooling rates relative to those associated with heating.

Figure 14A:
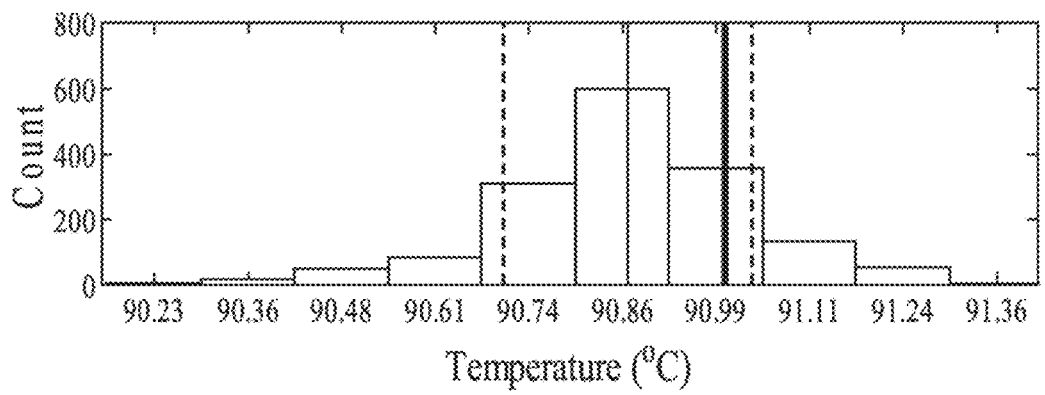
FIGS. 14A to 14C are histograms showing the temperature variation of the PCR solution at the temperatures: 91° C., 55° C. and 72° C., respectively, wherein the solid grey lines are placed at the target temperatures; the darker solid lines are located at the average temperatures; and the dashed lines are located one (sample) standard deviation away from the corresponding average.
Figure 14B:
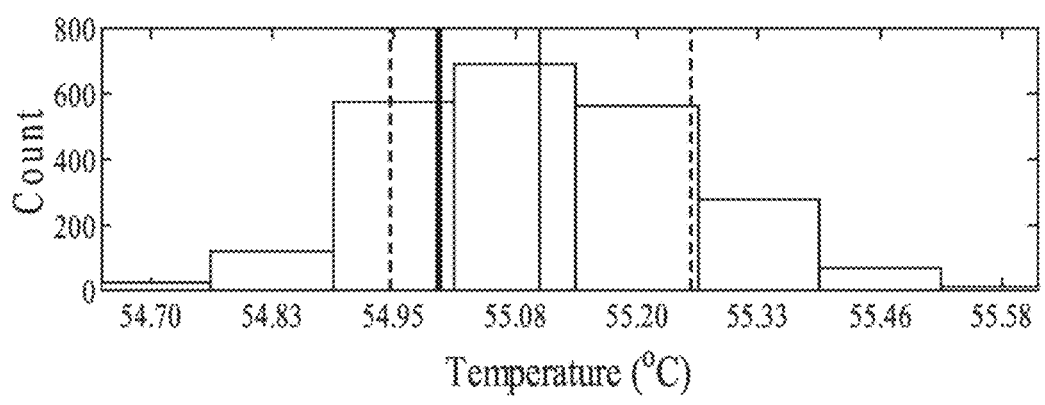
Figure 14C:
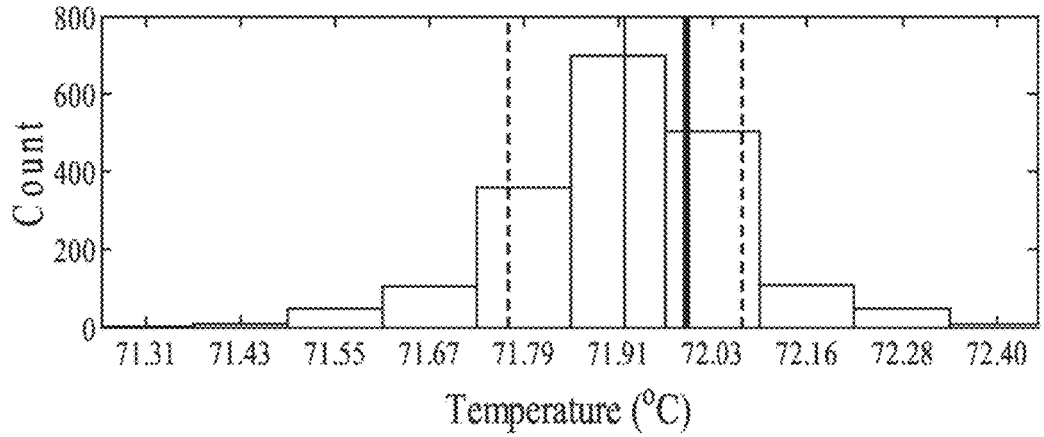

Temperature stability of the instrument was also determined using the contact PCR data presented in FIG. 12. For each PCR step (denaturation, annealing, and elongation) all of the corresponding data points were aggregated. Averages and sample standard deviations were then computed (FIGS. 14A to 14C and Table 3). The results are 90.87±0.17° C. for denaturation (91° C. target), 55.10±0.16° C. for annealing (55° C. target), and 71.92±0.15° C. for elongation (72° C. target). The accuracy was determined by computing the fraction of data points that were at most one bit depth of the analog to digital converter away from the target temperature. The accuracy obtained was 22.2% for denaturing, 24.8% for annealing, and 26.6% for elongation, where accuracy is defined as the percentage of measurements that exactly hit the defined temperatures for each stage to within the accuracy of the analog to digital conversion of the measurement system.

FIGS. 14A to 14C demonstrate that the instrument is capable of maintaining a defined temperature within stabilities comparable to commercial instruments. The performance was compared to other PCR instruments, both open source and commercial. Table 4 summaries those instruments and the plasmonic thermocycler is capable of delivering similar or better stabilities than available instruments (Table 3).

TABLE 4

Comparison of commercially available PCR instruments

| Instrument | Stability ° C. | Ramp rate ° C. s$^{-1}$ |
| --- | --- | --- |
| Open PCR http://openpcr.org/the-machine/ | ±0.5 | 1 |
| Veriti thermocycler http://www.appliedbiosystems.com/absite/us/en/home/applications-technologies/pcr/thermal-cyclers.html | ±0.5 | 5 |
| Lightcycler 1536 https://www.roche-applied-science.com/sls/rtper/LC1536/index.jsp?id=LC1536_010000 | N/A | 4.8 |
| Thermo scientific arktik thermal cycler http://www.dharmacom.com | ±0.4 | 3 |
| Mx3005P QPCR system http://www.genomics.agilent.com | ±0.25 | 2.5 |
| Mastercycler ® pro S http://www.eppendorf.ca | ±0.3 | 6 |
| peqStar thermocycler http://www.peqlab.com/wcms/en/pdf/PEQLAB_peqSTAR2X.pdf | ±0.2 | 5 |

Of course, numerous modifications could be made to the embodiments above without departing from the scope of the invention as defined in the appended claims.

The invention claimed is:

1. A method of amplifying a nucleic acid molecule with a loop-mediated isothermal amplification (LAMP), through bulk heating a biological enzymatic reaction mixture in solution containing a nucleic acid template, a polymerase enzyme, and chemically modified nanoparticles comprising nanorods of metal, metallic coated organic nanotubes, or a combination thereof, having photo-thermal properties, to promote said LAMP, comprising:
(a) irradiating said chemically modified nanoparticles with an activation light beam from a continuous wave laser to provide excitation for a period of time to activate said photo-thermal properties of said chemically modified nanoparticles, such that said chemically modified nanoparticles release heat sufficient to provide said heating to the whole reaction mixture in solution and promote said LAMP.

2. The method according claim 1, wherein the nanoparticles are selected from the group consisting of carbon nanotubes coated with a metal and multiwalled carbon nanotubes coated with or decorated with a metal.

3. The method according to claim 2, wherein the metal is selected from the group consisting of Au, Ag, Pd, Pt, Fe, Cu, Al, and Zn.

4. The method according to claim 1, wherein said photo-thermal properties comprise a localized plasmon resonance at a surface of the chemically modified nanoparticles, and the activation light beam has a wavelength corresponding to said localized plasmon resonance.

5. The method according to claim 1, wherein the chemically modified nanoparticles are chemically modified by a chemical compound that prevents the inhibition of an active site of said polymerase enzyme.

6. The method according to claim 5, wherein the chemical compound that prevents the inhibition of the active site of said polymerase enzyme is polyethylene glycol.

7. The method according to claim 1, wherein the step of irradiating comprises adjusting a power of said activation light beam to regulate temperature of said biological enzymatic reaction mixture in solution through controlled heat release from said chemically modified nanoparticles.

8. The method according to claim 1, further comprising a step of monitoring said bulk heating, amplicon production, or both.

9. The method according to claim 8, wherein the step of monitoring said amplicon production comprises probing said chemically modified nanoparticles with a probing light beam, having a wavelength different than a wavelength of the activation light beam and coordinated with an absorption feature of said chemically modified nanoparticles spectrally separate from the photo-thermal properties used to release heat, to measure a change of an optical property of said chemically modified nanoparticles and correlate said change of the optical property with a change in said amplicon production.

10. The method according to claim 9, wherein said chemically modified nanoparticles have an elongated geometry, the wavelength of the activation light beam is coordinated with a longitudinal resonance of the nanoparticles and the wavelength of the probing light beam is coordinated with a transversal resonance of the nanoparticles.

11. The method of claim 1, comprising cooling of the reaction mixture after the heating thereof.

12. A method of amplifying a nucleic acid molecule with a loop-mediated isothermal amplification (LAMP) through bulk heating a biological enzymatic reaction mixture in solution containing
a nucleic acid template,
a polymerase enzyme,
first chemically modified nanoparticles comprising nanorods of metal, metallic coated organic nanotubes, or a combination thereof, having photo-thermal properties, to release heat and promote said LAMP, and
a second set of nanoparticles having an absorption feature spectrally separate from said photo-thermal properties of said first chemically modified nanoparticles,
comprising the steps of:
a) irradiating said first chemically modified nanoparticles with an activation light beam from a continuous wave laser to provide excitation for a period of time to activate said photo-thermal properties of said first chemically modified nanoparticles, such that said first chemically modified nanoparticles release heat sufficient to provide said heating to the whole reaction mixture in solution and promote said LAMP, and
b) monitoring said bulk heating, amplicon production, or both, by probing said second set of nanoparticles with a probing light beam having a wavelength different than a wavelength of the activation light beam and coordinated with said absorption feature.

13. The method of claim 12, wherein said second set of nanoparticles is second chemically modified nanoparticles comprising nanorods of metal, metallic coated organic nanotubes, or a combination thereof, having photo-thermal properties, and having an absorption feature spectrally separate from said photo-thermal properties of said first chemically modified nanoparticles.

14. The method of claim 1, wherein said nucleic acid template is from a cell, a virus or a bacteria.

15. The method of claim 1, further comprising the step of extracting said nucleic acid template from a cell, a virus or a bacteria prior to amplifying said nucleic acid molecule with LAMP.

16. The method of claim 15, wherein said step of extracting said nucleic acid template from a cell, a virus or a bacteria comprises irradiating said chemically modified nanoparticles with an activation light beam from a continuous wave laser to provide excitation for a period of time to activate said photo-thermal properties of said chemically modified nanoparticles, such that said chemically modified nanoparticles release heat sufficient for extraction of said nucleic acid template from said cell, virus or bacteria.

* * * * *

SEQUENCE LISTING

<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: Forward Primer

<400> SEQUENCE: 1
aaccagcccg actcctttg                                              19

<210> SEQ ID NO 2
<211> LENGTH: 20
<212> TYPE: DNA
<213> ORGANISM: Artificial Sequence
<220> FEATURE:
<223> OTHER INFORMATION: Reverse Primer

<400> SEQUENCE: 2
caggggccaa gtagagcatc                                             20